United States Patent
Thompson et al.

(10) Patent No.: US 10,441,192 B2
(45) Date of Patent: Oct. 15, 2019

(54) IMPEDANCE SHIFT DETECTION

(71) Applicant: St. Jude Medical, Cardiology Division, Inc., St. Paul, MN (US)

(72) Inventors: Cable Thompson, St. Paul, MN (US); Anthony D. Hill, Minneapolis, MN (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 0 days.

(21) Appl. No.: 15/649,839

(22) Filed: Jul. 14, 2017

(65) Prior Publication Data

US 2018/0014749 A1    Jan. 18, 2018

Related U.S. Application Data

(60) Provisional application No. 62/362,967, filed on Jul. 15, 2016.

(51) Int. Cl.
    *A61B 5/06*    (2006.01)
(52) U.S. Cl.
    CPC ............... *A61B 5/061* (2013.01); *A61B 5/062* (2013.01); *A61B 5/063* (2013.01); *A61B 5/064* (2013.01); *A61B 5/066* (2013.01)
(58) Field of Classification Search
    USPC ........................................................ 382/128
    See application file for complete search history.

(56) References Cited

U.S. PATENT DOCUMENTS

| | | |
|---|---|---|
| 2011/0158488 A1 | 6/2011 | Cohen et al. |
| 2011/0288615 A1 | 11/2011 | Armstrong et al. |
| 2012/0053422 A1* | 3/2012 | Rantala ............. A61B 5/02055 600/300 |
| 2012/0265054 A1* | 10/2012 | Olson ................. A61B 5/6852 600/424 |

(Continued)

OTHER PUBLICATIONS

Eberly, David, "Distance from a Point to an Ellipse, an Ellipsoid, or a Hyperellipsoid," Geometric Tools, Redmond WA 98052, https://www.geometrictools.com/, Created: Jun. 28, 2013; Last Modified: Sep. 28, 2018.

*Primary Examiner* — Justin P. Misleh
(74) *Attorney, Agent, or Firm* — Dykema Gossett PLLC (57) ABSTRACT

A pre-shift set of fiducials each including a pre-shift fiducial impedance location and a pre-shift fiducial magnetic location can be determined. The pre-shift fiducial impedance locations and the pre-shift fiducial magnetic location are associated with a medical device. A post-shift set of fiducials each including a post-shift fiducial impedance location and a post-shift fiducial magnetic location can be determined. The post-shift fiducial impedance locations and the post-shift fiducial magnetic locations are associated with the medical device. A pre-shift transformation can be fit to the pre-shift set of fiducials and a post-shift transformation can be fit to the post-shift set of fiducials. A determination can be made whether the pre-shift transformation differs from the post-shift transformation. An indication that an impedance shift has occurred between the pre-shift set of fiducials and the post-shift set of fiducials can be generated based on the difference between the pre-shift transformation and the post-shift transformation.

16 Claims, 4 Drawing Sheets

(56) References Cited

U.S. PATENT DOCUMENTS

| | | | |
|---|---|---|---|
| 2013/0066193 A1* | 3/2013 | Olson | A61B 5/062 600/424 |
| 2014/0257047 A1* | 9/2014 | Sillay | A61B 5/11 600/301 |
| 2015/0045666 A1 | 2/2015 | Lynn | |
| 2015/0157273 A1 | 6/2015 | An et al. | |
| 2016/0367168 A1 | 12/2016 | Malinin et al. | |
| 2017/0030990 A1* | 2/2017 | Janich | A61B 5/055 |

* cited by examiner

IMPEDANCE SHIFT DETECTION

CROSS-REFERENCE TO RELATED APPLICATION

This application claims priority to U.S. provisional patent application No. 62/362,967 entitled "IMPEDANCE SHIFT DETECTION," filed 15 Jul. 2016, which is hereby incorporated by reference as though fully set forth herein.

BACKGROUND a. Field

The present disclosure relates generally to impedance shift detection.

b. Background

The three-dimensional coordinates of a catheter or other medical device moving within a patient's body are often tracked using a localization system (sometimes also referred to as a "mapping system," "navigation system," or "positional feedback system"). These devices typically use magnetic, electrical, ultrasound, and other radiation sources to determine the coordinates of these devices. For example, impedance-based localization systems determine the coordinates of the medical device by interpreting a voltage measured by the medical device as a location within an electrical field.

Each different type of localization system offers certain advantages and, disadvantages. For example, an impedance-based localization system offers the ability to track numerous localization elements simultaneously, but is susceptible to inhomogeneities in the electrical field and shift resulting from varying impedance regions and other external factors. Likewise, a magnetic-based system offers the advantages of improved homogeneity and less shift than an impedance-based system. Such systems, however, require special sensors to be used as localization elements and, as such, are relatively limited in the number of localization elements that can be simultaneously tracked.

SUMMARY

Various embodiments herein provide a method for detection of an impedance shift. A pre-shift set of fiducials that includes for each fiducial a pre-shift fiducial impedance location and a pre-shift fiducial magnetic location can be determined. The pre-shift fiducial impedance locations and the pre-shift fiducial magnetic locations are associated with a medical device. A post-shift set of fiducials that includes for each fiducial a post-shift fiducial impedance location and a post-shift fiducial magnetic location can be determined. The post-shift fiducial impedance locations and the post-shift fiducial magnetic locations are associated with the medical device. A pre-shift transformation can be fit to the pre-shift set of fiducials and a post-shift transformation can be fit to the post-shift set of fiducials. A determination can be made whether the pre-shift transformation differs from the post-shift transformation. An indication that an impedance shift has occurred between the pre-shift set of fiducials and the post-shift set of fiducials can be generated based on the difference between the pre-shift transformation and the post-shift transformation.

Various embodiments herein provide a system for determining a detection of an impedance shift. A pre-shift set of fiducial locations associated with a medical device can be determined. A post-shift set of fiducial locations associated with the medical device can be determined. A pre-shift transformation can be fit to the pre-shift set of fiducial locations and a post-shift transformation can be fit to the post-shift set of fiducial locations. A determination can be made, with a particular statistical confidence, whether the pre-shift transformation differs from the post-shift transformation by a particular threshold distance at a current location of the medical device. A determination can be made whether to generate an indication that an impedance shift has occurred, based on the particular statistical confidence of the determined difference.

DETAILED DESCRIPTION

Figure 1:
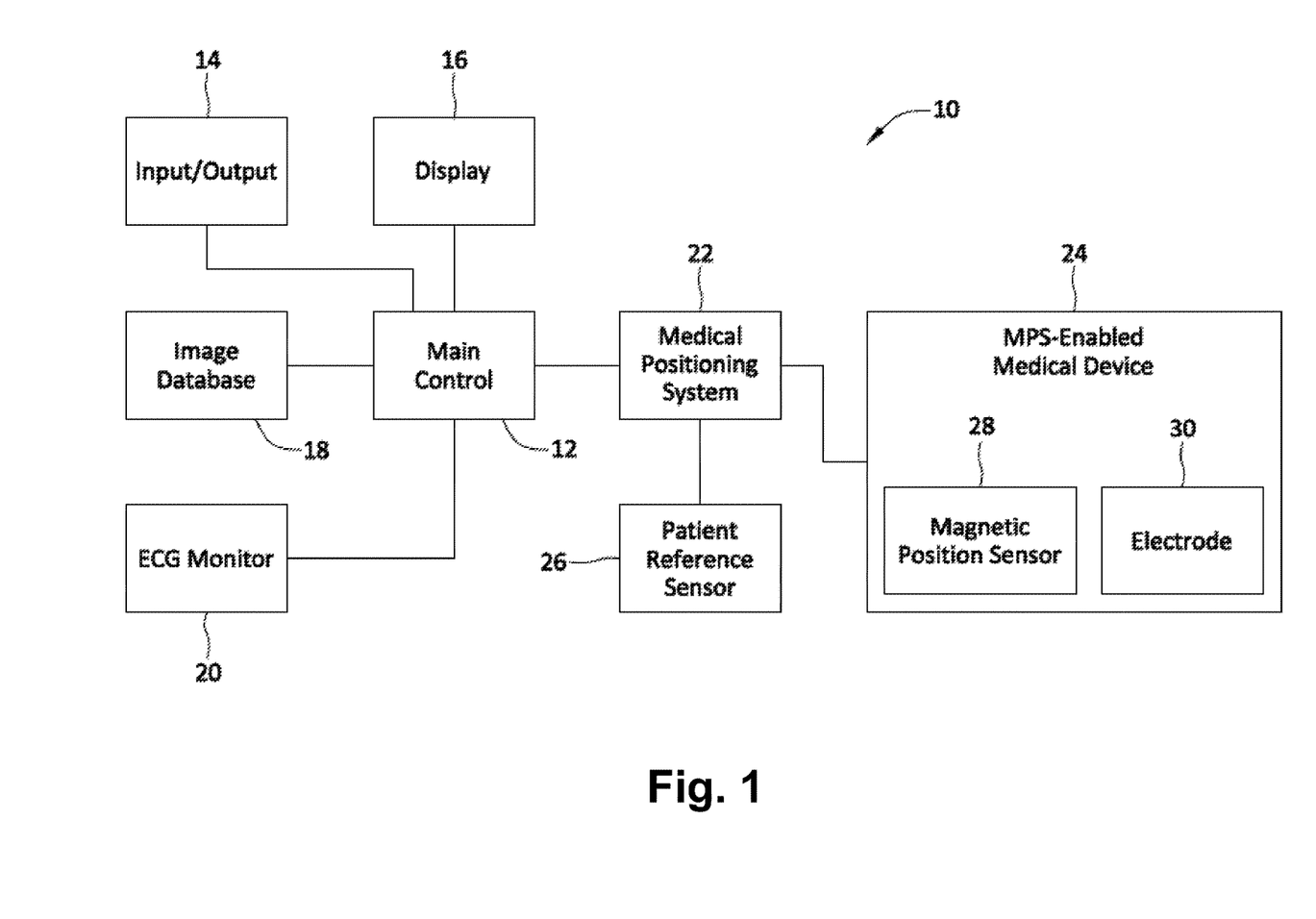
FIG. 1 depicts a schematic and block diagram view of a combined electromagnetic and impedance based navigation system, in accordance with embodiments of the present disclosure.

Referring now to the drawings wherein like reference numerals are used to identify identical or similar components in the various views, FIG. 1 is a diagrammatic view of a system 10 in which a medical device, such as a guidewire, catheter, introducer (e.g., sheath) incorporating a magnetic position sensor 28 and an electrode 30 may be used. FIG. 1 depicts a schematic and block diagram view of a combined electromagnetic and impedance based navigation system, in accordance with embodiments of the present disclosure.

Before proceeding to a detailed description of the embodiments of the present disclosure, a description of an exemplary environment in which such devices and sensors may be used will first be set forth. With continued reference to FIG. 1, system 10, as depicted, includes a main electronic control unit 12 (e.g., a processor) having various input/output mechanisms 14, a display 16, an optional image database 18, an electrocardiogram (ECG) monitor 20, a localization system, such as a medical positioning system 22, a medical positioning system-enabled elongate medical device 24, a patient reference sensor 26, a magnetic position sensor 28 and an electrode 30. The system 10 can be an EnSite™ Precision™ cardiac mapping system, in some embodiments, which can include a combination of electromagnetic and impedance based navigational systems. The electrode 30 can provide measurements associated with localization measurements and/or electrogram (EGM) measurements. For simplicity, one magnetic position sensor 28 and one electrode 30 are shown, however, more than one magnetic position sensor 28 and/or more than one electrode 30 can be included in the system 10.

Input/output mechanisms 14 may comprise conventional apparatus for interfacing with a computer-based control unit including, for example, one or more of a keyboard, a mouse, a tablet, a foot pedal, a switch and/or the like. Display 16 may also comprise conventional apparatus, such as a computer monitor.

Various embodiments described herein may find use in navigation applications that use real-time and/or pre-acquired images of a region of interest. Therefore, system 10 may optionally include image database 18 to store image information relating to the patient's body. Image information may include, for example, a region of interest surrounding a destination site for medical device 24 and/or multiple regions of interest along a navigation path contemplated to be traversed by medical device 24. The data in image database 18 may comprise known image types including (1) one or more two-dimensional still images acquired at respective, individual times in the past; (2) a plurality of related two-dimensional images obtained in real-time from an image acquisition device (e.g., fluoroscopic images from an x-ray imaging apparatus), wherein the image database acts as a buffer (live fluoroscopy); and/or (3) a sequence of related two-dimensional images defining a cine-loop wherein each image in the sequence has at least an ECG timing parameter associated therewith, adequate to allow playback of the sequence in accordance with acquired real-time ECG signals obtained from ECG monitor 20. It should be understood that the foregoing embodiments are examples only and not limiting in nature. For example, the image database may also include three-dimensional image data as well. It should be further understood that the images may be acquired through any imaging modality, now known or hereafter developed, for example X-ray, ultra-sound, computerized tomography, nuclear magnetic resonance or the like.

ECG monitor 20 is configured to continuously detect an electrical timing signal of the heart organ through the use of a plurality of ECG electrodes (not shown), which may be externally-affixed to the outside of a patient's body. The timing signal generally corresponds to a particular phase of the cardiac cycle, among other things. Generally, the ECG signal(s) may be used by the control unit 12 for ECG synchronized play-back of a previously captured sequence of images (cine loop) stored in database 18. ECG monitor 20 and ECG-electrodes may both comprise conventional components.

Medical positioning system 22 is configured to serve as the localization system and therefore to determine position (localization) data with respect to one or more magnetic position sensors 28 and/or electrodes 30 and output a respective location reading. The location readings may each include at least one or both of a position and an orientation (P&O) relative to a reference coordinate system (e.g., magnetic based coordinate system, impedance based coordinate system), which may be the coordinate system of MPS 22. For some types of sensors, the P&O may be expressed with five degrees-of-freedom (five DOF) as a three-dimensional (3D) position (e.g., a coordinate in three perpendicular axes X, Y and Z) and two-dimensional (2D) orientation (e.g., a pitch and yaw) of a magnetic position sensor 28 in a magnetic field relative to a magnetic field generator(s) or transmitter(s) and/or electrode 30 in an applied electrical field relative to an electrical field generator (e.g., a set of electrode patches). For other sensor types, the P&O may be expressed with six degrees-of-freedom (six DOF) as a 3D position (e.g., X, Y, Z coordinates) and 3D orientation (e.g., roll, pitch, and yaw).

Medical positioning system 22 determines respective locations (e.g., P&O) in the reference coordinate system based on capturing and processing signals received from the magnetic position sensor 28 while the sensor is disposed in a controlled low-strength alternating current (AC) magnetic (e.g., magnetic) field and signals received from the electrode 30 while the electrodes are disposed in a controlled electrical field generated by electrode patches, for example.

Each magnetic position sensor 28 and the like may comprise a coil and, from an electromagnetic perspective, the changing or AC magnetic field may induce a current in the coil(s) when the coil(s) are in the magnetic field. The magnetic position sensor 28 is thus configured to detect one or more characteristics (e.g., flux) of the magnetic field(s) in which it is disposed and generate a signal indicative of those characteristics, which is further processed by medical positioning system 22 to obtain a respective P&O for the magnetic position sensor 28. The electrode 30 may comprise a ring electrode, in some examples. The electrode 30 can be configured to detect one or more characteristics (e.g., current) of the electrical field(s) in which it is disposed and generate a signal indicative of those characteristics, which is further processed by medical positioning system 22 to obtain a respective P&O for the plurality of electrodes 30.

Referring still to FIG. 1, in an embodiment, medical positioning system 22 may determine the P&O of medical positioning system enabled medical device 24 according to certain physical characteristics of electromagnetic position sensor 28 and electrode 30 in addition to the signals received from magnetic position sensor 28 and electrode 30. Such characteristics may include predetermined calibration data, for example, indicative of or corresponding to the respective winding angles of one or more portions of a coil on sensor 28, the number of coil portions, the type(s) of conductor used in the coil, and the direction and number of loops in the coil. In addition, such characteristics may include predetermined calibration data, for example, indicative of or corresponding to a position of electrode 30, the number of electrodes 30, size of electrode 30, shape of electrode 30, and type of material(s) of which the electrodes are formed. Medical positioning system 22 may have such characteristics of the magnetic position sensor 28 and/or electrode 30 pre-programmed, may determine such characteristics from a calibration procedure, or may receive such characteristics from a storage element coupled with medical device 24.

Magnetic position sensor 28 and the electrode 30 may be associated with medical positioning system enabled medical device 24. Another medical positioning system sensor, namely, patient reference sensor (PRS) 26 (if provided in system 10) can be configured to provide a positional reference of the patient's body so as to allow motion compensation for patient body movements, such as respiration-induced movements. Such motion compensation is described in greater detail in U.S. Patent Publication No. 2011/0158488, entitled "Compensation of Motion in a Moving Organ Using an Internal Position Reference Sensor", hereby incorporated by reference in its entirety as though fully set forth herein. PRS 26 may be attached to the patient's manubrium sternum or other location. Like the magnetic position sensor 28, PRS 26 can be configured to detect one or more characteristics of the magnetic field in which it is disposed, wherein medical positioning system 22 determines a location reading (e.g., a P&O reading) indicative of the PRS's position and orientation in the reference coordinate system. In some embodiments, an additional PRS can be configured to detect one or more characteristics of the electrical field in which it is disposed, wherein the medical positioning system 22 determines a location reading (e.g., a P&O reading) indicative of the PRS's position and orientation in the reference coordinate system.

Embodiments of the present disclosure can detect impedance shift, associated with the electrode 30. For example, impedance-based navigational systems can be subject to nonlinear shift due to numerous physiologic phenomena (e.g., local conductivity changes due to saline or lesions, sweat/patch interactions, changes in lung filling, etc.). Magnetic navigational systems are not subject to these phenomena. A determination of whether an impedance shift exists can be determined by collecting a pre-shift set of fiducials (e.g., pre-shift fiducial data set) and a post-shift set of fiducials (e.g., post shift fiducial data set). A pre-shift transformation can be fit to the pre-shift set of fiducials and a post-shift transformation can be fit to the post-shift set of fiducials. A determination of whether an impedance shift has occurred can be made based on whether a statistical confidence exists that the pre-shift transformation differs from the post-shift transformation by a distance threshold, as further discussed herein.

Use of impedance based electrodes in an electric localization field can be associated with inherent inhomogeneities (e.g., shift). Embodiments of the present disclosure can provide detection of shift associated with the impedance based device, to provide for an indication of accuracy at which the medical device is being navigated.

Figure 2:
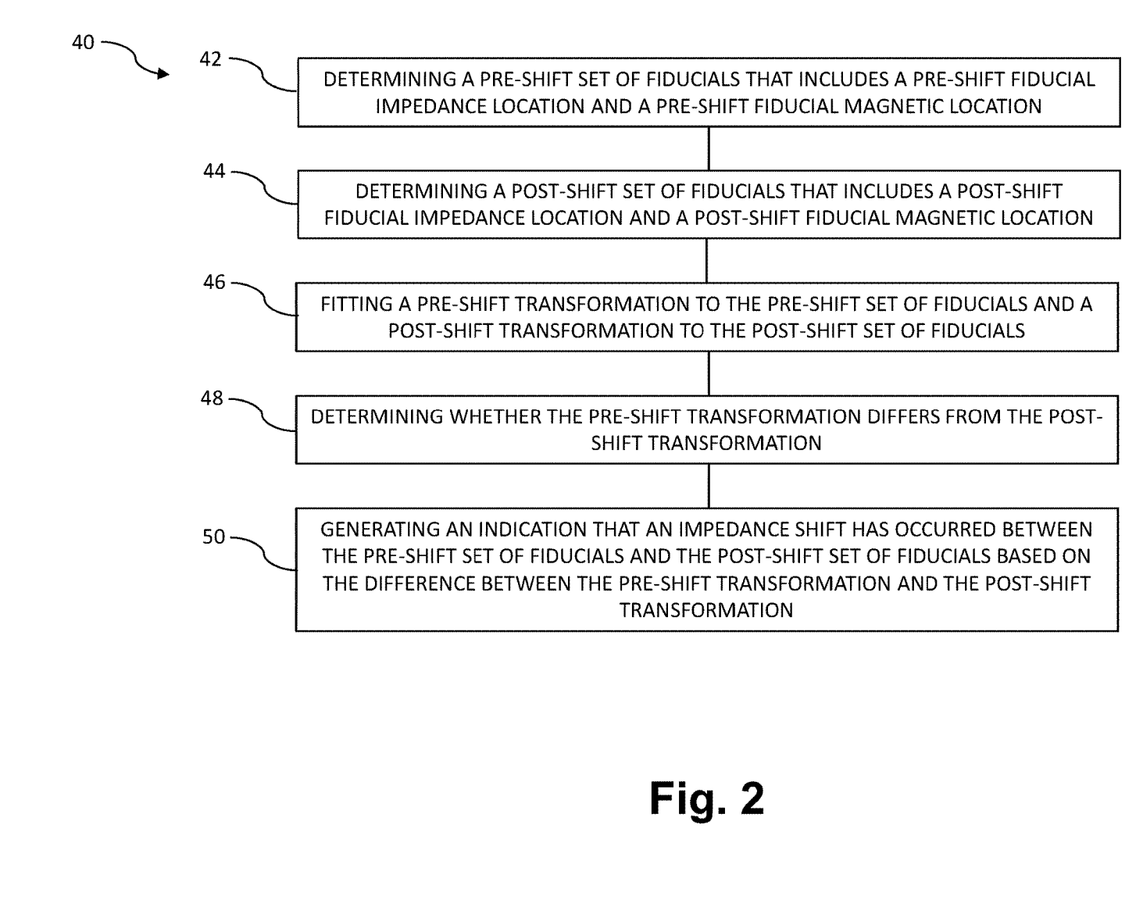
FIG. 2 depicts a method flow diagram associated with impedance shift detection, in accordance with embodiments of the present disclosure.

FIG. 2 depicts a method flow diagram 40 associated with impedance shift detection, in accordance with embodiments of the present disclosure. As discussed herein, the medical positioning system 22 can generate an electrical field in which the electrode 30 can be placed. The electrode 30 can generate an impedance signal based on the strength of the electrical field and the position of the electrode 30 in the electrical field. Based on the impedance signal, the impedance location of the electrode 30 can be determined in an impedance based coordinate system. The medical positioning system 22 can also generate a magnetic field in which the magnetic position sensor 28 can be placed. The magnetic location of the magnetic position sensor 28 can be computed based on a signal received from the magnetic position sensor 28. The signal can be generated by the magnetic position sensor 28 based on the strength of the magnetic field and the position and/or orientation of the magnetic position sensor 28 in the magnetic field.

In some embodiments, the method can include determining a set of fiducial points. For example, the method can include determining a pre-shift set of fiducials that includes for each fiducial a pre-shift fiducial impedance location and a pre-shift fiducial magnetic location, at block 42. The set of fiducial points can be those used, for example, in magnetic field scaling or an electromagnetic dynamic registration, as further discussed in U.S. application Ser. No. 15/187,286, entitled "Electromagnetic Dynamic Registration for Device Navigation," which is hereby incorporated by reference as though fully set forth herein. In some embodiments, the pre-shift fiducial impedance locations and the pre-shift fiducial magnetic locations can be associated with a medical device (e.g., medical device 24).

Figure 3:
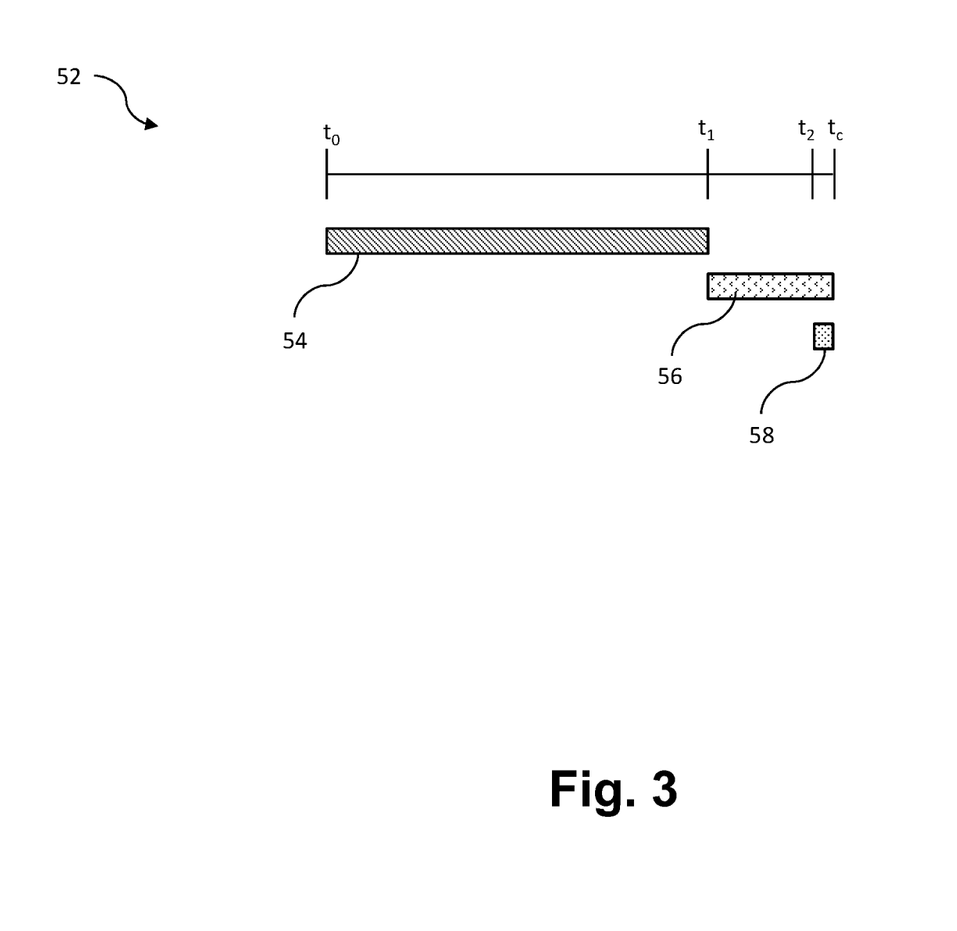
FIG. 3 depicts a time scale associated with a pre-shift time period, a post shift time period, and a magnetic location time period.

The pre-shift set of fiducials can be collected during a pre-shift time period, further discussed in relation to FIG. 3. The pre-shift set of fiducials can serve as a baseline, against which a determination can be made whether any impedance shift has occurred.

In some embodiments, the pre-shift time period can exclude a most recent time period. The most recent time period can be in a range from 5 to 300 seconds, in some embodiments. In some embodiments, the most recent time period can be in a range from 10 to 30 seconds. In some embodiments, the most recent time period can be from 5 to 10 seconds, 5 to 30 seconds, or 10 to 300 seconds. However, the pre-shift time period can be less than 5 seconds or greater than 30 seconds, in some embodiments. For example, the pre-shift fiducial impedance locations and the pre-shift fiducial magnetic locations can be collected over a particular time period that excludes the most recent time period (e.g., the last 10 seconds). If the most recent time period is too short, there may not be enough data that is collected to detect a shift. However, if the most recent time period is too long, the system may not be received as responsive. In some embodiments, the pre-shift set of fiducials can be continuously collected, however the pre-shift fiducial impedance locations and the pre-shift fiducial magnetic locations collected over the most recent time period can be excluded from any further calculations. Alternatively, in some embodiments, the pre-shift set of fiducials can be collected over a time period that excludes the most recent time period.

The method can include determining a post-shift set of fiducials that includes for each fiducial a post-shift fiducial impedance location and a post-shift fiducial magnetic location, at block 44. The post-shift fiducial impedance locations and the post-shift fiducial magnetic locations can be associated with the medical device. In some embodiments, the post-shift set of fiducials can be collected during a post-shift time period, further discussed in relation to FIG. 3. The post-shift time period can include a time period that abuts a current time (e.g., a most recent time period, as previously discussed).

In some embodiments, a location associated with magnetic position sensors can be collected over a magnetic location time period, further discussed in relation to FIG. 3, to provide a current location of the medical device. In some embodiments, the magnetic location time period can be shorter than the post-shift time period and/or can overlap the post-shift time period, in some embodiments. The magnetic location time period can abut a current time and can range in time from 0.01 to 5 seconds, in some embodiments. However, the magnetic location time period can be less than 0.01 seconds or greater than 5 seconds, in some embodiments. In an example, the magnetic location time period can be a 1 second length of time prior to and abutting the current time.

In some embodiments, pre-processing and/or filtering steps can be performed on the pre-shift set of fiducials and/or the post-shift set of fiducials. While pre-processing and/or filtering steps can be performed to both the pre-shift set of fiducials and/or the post-shift set of fiducials, for simplicity, the below discussion is made with reference to the pre-shift set of fiducials. In the collection of the pre-shift set of fiducials, data points that make up the pre-shift set of fiducials can be filtered based on bad status bits. If a determination is made that one or more fiducials within the pre-shift set of fiducials includes bad status bits, those fiducials can be filtered out and not used in further determination of impedance shift. Bad status bits can include data of poor quality, for example, data subject to synchronization errors, data from electrodes being used for stim, data collected from a sensor disposed in a magnetic field, which has been distorted (e.g., via a metallic object), data received from a broken sensor, and/or other data obtained from a position sensor, which can be unreliable. In some embodiments, bad status bits can refer to a union of data acquisition errors that may be detected in hardware and/or data quality indicators that have been detected in software (e.g., filter settling, excessive velocity of a catheter, in-sheath electrodes, ventilator gating, etc.). For impedance localization, examples of bad status bits can be patches that have been disconnected, in-sheath electrodes, excessive noise, saturation prior to demodulation and/or excessive velocity of a catheter. For magnetic localization, examples of bad status bits can be poor convergence, movement of a magnetic position sensor out of a motion box, and/or metal distortion caused to the magnetic field.

In some embodiments, the pre-shift set of fiducials can be gated for a particular respiratory phase. The ventilatory cycle can cause intracardiac catheters (e.g., medical devices) to experience motion, resulting in correlated changes in the reported positions in both impedance and magnetic coordinate systems. Simultaneously, the ventilatory cycle can introduce artifacts into both magnetic and impedance coordinate systems that are uncorrelated with each other. For example, an anterior PRS rises, falls and tilts as the patient breathes, resulting in artifacts in a PRS-referenced coordinate system. The navigational currents of the impedance coordinate system can be changed as the lungs empty and fill, resulting in artifacts in the impedance coordinate system. To compute a registration that is not corrupted by ventilatory artifact, fiducial collection can be gated to a signal responsive to the ventilatory phase. If gating operates without error, fiducials can be collected in a standard ventilatory phase. In some embodiments, spatial and temporal basis functions can be used rather than gating, as described in U.S. application Ser. No. 15/187,286, entitled "Electromagnetic Dynamic Registration for Device Navigation," hereby incorporated by reference in its entirety as though fully set forth herein.

FIG. 3 depicts a time scale 52 associated with a pre-shift time period 54, a post-shift time period 56, and a magnetic location time period 58. As depicted, the pre-shift time period 54 is depicted as extending from $t_0$ to $t_1$, with a time period equal to $t_1$-$t_0$. The pre-shift time period 54 can be in a time period in a range from 10 seconds to 30 minutes. In some embodiments, the period can be over 30 minutes. In some embodiments, the pre-shift time period may not be a contiguous interval of time. Where magnetic field scaling is performed, a number of fiducials from the magnetic field scaling can be used to create a pre-shift set of fiducials. In some embodiments, a user can remove data from selected areas and/or times periods. In some embodiments, the post-shift time period 56 can include a time period extending from $t_1$ to a current time $t_c$, with a time period equal to $t_c$-$t_1$. In some embodiments, as depicted, the pre-shift time period 54 and the post-shift time period 56 are mutually exclusive with respect to one another. However, in some embodiments, the pre-shift time period 54 and the post-shift time period 56 can overlap. In some embodiments, the magnetic location time period 58 can include a time period extending from $t_2$ to $t_c$, with a time period equal to $t_c$-$t_0$. As depicted and discussed herein, the magnetic location time period 58 can overlap the post-shift time period 56. However, in some embodiments, the magnetic location time period 58 and the post-shift time period 56 can be mutually exclusive. While the pre-shift time period 54 is depicted as having a greater time period than the post-shift time period 56, the post-shift time period 56 can have a time period that is equal to or greater than the pre-shift time period 54.

With further reference to the method flow diagram 40, in some embodiments, the method can include fitting a pre-shift transformation to the pre-shift set of fiducials and a post-shift transformation to the post-shift set of fiducials, at block 46. The transformations can be based on magnetic-to-impedance mapping, rather than impedance-to-magnetic mapping. The transformation can be based on magnetic-to-impedance mapping because the magnetic based coordinates can be considered as stable and can be used as a stable "ground truth" comparison with the impedance based coordinates to detect when the impedance field changes (e.g., a shift occurs). In addition, when mapping from magnetic-to-impedance, the transformation can be reliably limited to harmonic functions, while that is not necessarily the case with mapping from impedance-to-magnetic. In some embodiments, each transformation can include a confidence interval, as further discussed herein.

In some embodiments, the pre-shift transformation and the post-shift transformation can be constructed by determining transformation pairs for the pre-shift set of fiducials (e.g., data set) and the post-shift set of fiducials (e.g., data set), in accordance with the below transformation function $$\phi w(x) = \sum_i w_i^T b_i(x),$$

where the transformation function has coefficients ("weights") W. W can be a j×3 matrix for j, the number of basis functions, and each row $w_i$ of W can be represented as $<x_i, y_i, z_i>$, indicating how much basis function "i" contributes to the x, y, and z components of the transformation. The coefficients W can be parameters that determine how the transformation function maps magnetic space to impedance space. In an example, W can be a registration between magnetic space and impedance space. Here, b is a function mapping magnetic coordinates to a vector of basis function values, for a basis function set such as a Thin Plate Splines basis, Procrustes basis, b-spline basis, non-uniform rational B-spline (NURBS) basis, power series basis, power series basis constrained to span only harmonic functions, principal component analysis of measured magnetic-to-impedance transformations, or any other set of linearly combinable basis functions. One particularly useful basis function can be Thin Plate Splines, which uses a spline-based technique for both smoothing and data interpolation. In some embodiments, the use of Thin Plate Splines basis can be preferred. In subsequent notation discussed herein, let $B_x$ be a matrix whose i-th row is $b(x)^T$. Then, for a set of "pre-shift" coefficients $\overleftarrow{W}$ and "post-shift" coefficients $\overrightarrow{W}$, call ($\emptyset_{\overleftarrow{W}}$, $\emptyset_{\overrightarrow{W}}$) a "transformation pair." In some embodiments, in what follows, a transformation pair will be considered to be based upon a pre-shift fiducial data set (e.g., pre-shift set of fiducial locations) ($\overleftarrow{X}$, $\overleftarrow{Y}$) and a post-shift fiducial data set (e.g., post-shift set of fiducial locations) ($\overrightarrow{X}$,$\overrightarrow{Y}$).

In some embodiments, the method 40 can include determining whether the pre-shift transformation differs from the post-shift transformation, at box 48. For example, the method 40 can include determining, with a particular statistical confidence, whether the pre-shift transformation differs from the post-shift transformation by a particular threshold distance at a current location of a medical device. In some embodiments of the present disclosure, the particular threshold distance can be a user-configurable threshold distance, which can be a distance in a range from 1 millimeter to 20 millimeters. In some embodiments the particular threshold distance can be a distance in a range from 2 millimeters to 10 millimeters. However, the user-configurable threshold distance can be less than 1 millimeter or greater than 20 millimeters. In an example, the user-configurable threshold distance can be 5 millimeters. If the impedance shift (if any) between the pre-shift transformation and the post-shift transformation exceeds the threshold distance, the shift can be deemed clinically significant and reported to a user, as further discussed herein. The particular statistical confidence threshold can be user configurable. In some embodiments, the particular statistical confidence threshold can be in a range from 90% to 99.99%. In some embodiments, the statistical confidence threshold can be in a range from 95% to 99.9%. In an example, the particular statistical confidence can be set to a 99% confidence interval that the pre-shift transformation does not differ from the post-shift transformation by more than the particular threshold distance. In determining whether or not a transformation pair (e.g., pre-shift transformation and post-shift transformation) is shifted, a norm of the difference between a pair of transformations ($\emptyset_{\overleftarrow{W}}$, $\emptyset_{\overrightarrow{W}}$) at a set of current (or otherwise relevant) catheter locations X* in magnetic coordinates can be defined as:

$$r^2_{\phi_{\overleftarrow{W}}, \phi_{\overrightarrow{W}}}(X^*) = (\overleftarrow{W} - \overrightarrow{W})^T B_{X^*}{}^T B_{X^*}(\overleftarrow{W} - \overrightarrow{W})$$

X* can be a matrix where each row is a magnetic location at which a shift can be detected. In some embodiments, the magnetic location can be a magnetic location measured in the magnetic location time period, which in an example can be 1 second, as previously discussed. If a distance $\epsilon$ is considered to represent a minimal clinically significant shift, then a transformation pair can be considered to be unshifted, if:

$$r^2_{\phi_{\overleftarrow{W}}, \phi_{\overrightarrow{W}}}(X^*) \leq \beta$$

where $\beta = n\epsilon^2$, n is the number of points in X*, and where E represents the distance threshold for a clinically significant shift, as previously discussed. The above metric of shift size can be used in part to enable a numerical method, further discussed below, by making the set of unshifted transformation pairs ellipsoidal.

In some embodiments, to test whether an impedance shift has occurred, the following assumptions can be made about the pre-shift fiducial data set ($\overleftarrow{X}$, $\overleftarrow{Y}$) and the post-shift fiducial data set ($\overrightarrow{X}$, $\overrightarrow{Y}$). For example, an assumption can be made that there exists unknown coefficients $\overleftarrow{W}$ and $\overrightarrow{W}$ and a measurement covariance $\Sigma$, such that for all i, $$\overleftarrow{y}_i = \emptyset_{\overleftarrow{W}}(\overleftarrow{x}_i) + \overleftarrow{n}_i, \overleftarrow{n}_i \sim \mathcal{N}(0, \Sigma)$$

$$\overrightarrow{y}_i = \emptyset_{\overrightarrow{W}}(\overrightarrow{x}_i) + \overrightarrow{n}_i, \overrightarrow{n}_i \sim \mathcal{N}(0, \Sigma)$$

The notation $\mathcal{N}(0, \Sigma)$, indicates that n's are normally distributed with covariance sigma (i.e., an assumption can be made that the data includes an unknown amount of white noise, and otherwise is well described by the transformation $\emptyset_W$). The following hypotheses can be distinguished, based on the data ($\overleftarrow{X}$, $\overleftarrow{Y}$), ($\overrightarrow{X}$, $\overrightarrow{Y}$):

$H_0$: $r^2_{\phi_{\overleftarrow{W}}, \phi_{\overrightarrow{W}}}(X^*) \leq \beta$ (Null hypothesis)

$H_1$: $r^2_{\phi_{\overleftarrow{W}}, \phi_{\overrightarrow{W}}}(X^*) < \beta$ (Alternative hypothesis)

$H_0$ is a statement that ($\emptyset_{\overleftarrow{W}}$, $\emptyset_{\overrightarrow{W}}$) is an unshifted transformation pair. In some embodiments, by statistically refuting $H_0$, then a declaration that a shift is detected can be made.

A consistency of measurements with a fixed set of coefficients can be determined via Hotelling's $T^2$ test. In some embodiments, Hotelling's $T^2$ test can be used to compare measurements to a set of hypothesized regression weights. One set of "old" weights and another of "new" weights can be assumed and the weights can be optimized to minimize $t^2$ (e.g., test statistic $\tau$, as further discussed herein), which assumes a fixed set of weights and indicates whether the data is consistent with those weights, subject to an "insignificant shift" constraint. The "insignificant shift" constraint can be defined as a size of an impedance shift that is less than the distance threshold deemed clinically significant. The Hotelling's $T^2$ test statistic can be represented as:

$$t^2_{\phi_{\overleftarrow{W}}, \phi_{\overrightarrow{W}}}(\overleftarrow{X}, \overleftarrow{Y}, \overrightarrow{X}, \overrightarrow{Y}) = \frac{(B^+ Y - W)^T B^T B (B^+ Y - W)}{k \hat{\sigma}^2}$$

where $B^+$ denotes the Moore-Penrose pseudoinverse of B, k/3 is the number of columns of B, and $$B = \begin{bmatrix} B_{\overleftarrow{X}} & 0 \\ 0 & B_{\overrightarrow{X}} \end{bmatrix}$$

$$Y = \begin{bmatrix} \overleftarrow{Y} \\ \overrightarrow{Y} \end{bmatrix}$$

$$W = \begin{bmatrix} \overleftarrow{W} \\ \overrightarrow{W} \end{bmatrix}$$

$$\hat{\sigma}^2 = \frac{tr(Y^T(Y - BB^+)^T(Y - BB^+)Y)}{n - k}$$

with n/3 being the number of rows of Y. In some embodiments where the fiducial data sets ($\overleftarrow{X}$, $\overleftarrow{Y}$) and ($\overrightarrow{X}$, $\overrightarrow{Y}$) have been temporally low-pass filtered with a cutoff frequency $\lambda$ and a data rate of d samples per time (e.g., d samples per second), the definition of $\hat{\sigma}$ can be multiplied by $$\frac{d}{2\lambda}$$

to account for this.

Computing a minimum $t^2$ can be equivalent to solving a point-to-hyperellipsoid distance problem. In some embodiments, the minimum $t^2$ (e.g., test statistic $\tau$) for a consistency of measurements associated with the null hypothesis $H_0$, as discussed herein, can be represented as $$\tau(\overleftarrow{X}, \overleftarrow{Y}, \overrightarrow{X}, \overrightarrow{Y}) = \min_{\overleftarrow{W}, \overrightarrow{W} \text{ s.t. } r^2_{\overleftarrow{W}, \overrightarrow{W}}(X^*) \leq \beta} t^2_{\phi_{\overleftarrow{W}}, \phi_{\overrightarrow{W}}}(\overleftarrow{X}, \overleftarrow{Y}, \overrightarrow{X}, \overrightarrow{Y})$$

In some embodiments, to determine whether a statistical confidence exists that the pre-shift data set and the post-shift data set differ by more than the above referenced distance threshold at a current location of a medical device (e.g., determined via the magnetic position sensor associated with the medical device) or other locations of interest; a shift detection threshold model can be run periodically or continuously. The model can be represented:

$$F(x; k, n-k) = I_{\frac{kx}{kx+n-k}}\left(\frac{k}{2}, \frac{n-k}{2}\right),$$

which is Sendecor's F-distribution, where I is a regularized incomplete beta function. Evaluating the complement cumulative distribution function of $F_{n-k}{}^k$ at $\tau(\overleftarrow{X}, \overleftarrow{Y}, \overrightarrow{X}, \overrightarrow{Y})$ (i.e., evaluating p=1−F($\tau$; k, n−k)), gives a p-value that upperbounds the probability of measuring fiducial data sets as extreme as $(\bar{\mathbf{X}}, \bar{\mathbf{Y}})$ and $(\vec{X}, \vec{Y})$ under the null hypothesis $H_0$. If this value is less than a statistical significance threshold $\alpha$, then a shift can be detected, in some embodiments. As discussed herein, the statistical significance threshold may or may not be user configurable. The statistical significance threshold can be in a range from 0.0001 to 0.1, and in an example can be 0.01. In some embodiments, the statistical significance threshold can be in a range from 0.05 to 0.001.

In some embodiments, the test statistic $\tau$ can be computed as a point-to-hyperellipsoid distance. The computation of the minimum $t^2$ value in determining the value of $\tau$, as referenced above, is nontrivial. The solution can be made easier through a change of variable. For example, using a singular value decomposition, let $$\frac{B_X^T B_X}{k\hat{\sigma}^2} = UDU^T,$$

so that U is orthogonal and D is diagonal. Then, let $$\Omega = D^{1/2} U^T W$$

$$\hat{\Omega} = D^{1/2} U^T B^+ Y$$

The $t^2$ statistic can be rewritten as $$t^2_{\phi_{\bar{W},\phi\vec{w}}}(\bar{\mathbf{X}}, \bar{\mathbf{Y}}, \vec{X}, \vec{Y}) = (\hat{\Omega} - \Omega)^T (\hat{\Omega} - \Omega)$$

which can be defined as the squared Euclidean distance between $\Omega$ and $\hat{\Omega}$. By letting $$\Psi = B_X U D^{-1/2},$$

the constraint $$r^2_{\phi_{\bar{W},\phi\vec{w}}}(X^*) \leq \beta$$

becomes $$\Omega^T \Psi^T \Psi \Omega \leq \beta,$$

which is a statement that $\Omega$ lies within a particular origin-centered hyperellipsoid. Thus, a computation is provided for the distance from $\hat{\Omega}$ to the closest point on or inside the ellipsoid $$\Omega^T \Psi^T \Psi \Omega \leq \beta.$$

If $\hat{\Omega}$ is inside the ellipsoid, the distance is zero; otherwise the point-to-hyperellipsoid distance problem can be solved by methods, such as those taught in Eberly, David. "Distance from a Point to an Ellipse, an Ellipsoid, or a Hyperellipsoid," www.geometrictools.com/Documentation/DistancePointEllipseEllipsoid.pdf. In implementing the point-to-ellipsoid distance calculation, care can be taken that it is robust to the cases where the hyperellipsoid's extent is zero or infinite along some of its principal axes. These cases can include instances where the hyperellipsoid is squashed flat (e.g., zero extent) or stretched out into a tube (e.g., infinite extent) along one or more of its principal axes.

In some embodiments, the method 40 can include generating an indication that an impedance shift has occurred between the pre-shift set of fiducials and the post-shift set of fiducials based on the difference between the pre-shift transformation and the post-shift transformation, at box 50. In an example, the method can include providing a notification to a user via a user interface that includes a common cause of the impedance shift. For example, common causes can include motion of the patient, medication that has been introduced into the patient, changes in bloodstream conductivity, movement of internal organs (e.g., changes in lung filling), local conductivity changes due to saline or lesions, sweat/patch interactions, etc. In some embodiments, the method can include providing a notification to the user via the user interface that includes ways to correct for the impedance shift. For example, ways to correct for the impedance shift can include applying a translational offset to impedance locations or rebuilding geometry models on which fiducial data sets are built (e.g., pre-shift fiducial data set), collecting additional location data to build a secondary electromagnetic registration to account for the detected shift. By alerting the user that determined locations of the medical device have changed due to an impedance shift, false clinical judgments can be prevented and the physicians can be allowed to quickly correct causes of impedance shift so they can continue on with a diagnosis and/or treatment of the patient.

In some embodiments, a time at which the impedance shift has occurred and/or a time at which an impedance shift was reported can be determined and/or stored in memory. To avoid alerting a user too often regarding the occurrence of an impedance shift, embodiments of the present disclosure can limit the reporting of the impedance shift to once over a particular time period and/or a recurring time period. For example, in some embodiments, if the impedance shift is reported and/or detected at time t', the impedance shift can be reported to the user. Upon reporting the impedance shift to the user, embodiments of the present disclosure can wait until time t", before resuming reporting of the detected impedance shifts to the user. In some embodiments, a minimum time interval between reported shifts can be a duration in a range from 45 seconds to 3 minutes. In other words, a time interval between t' and t" can be a duration of time ranging from 45 second to 3 minutes, although the time can be any range of time. In an example, the range of time can be 60 seconds. In some embodiments, the impedance shift can be reported over a recurring time period. For example, the impedance shift can be reported to the user once every 60 seconds, until the impedance shift does not exist or until a user interface receives a selection from a user to stop reporting the impedance shift.

Figure 4:
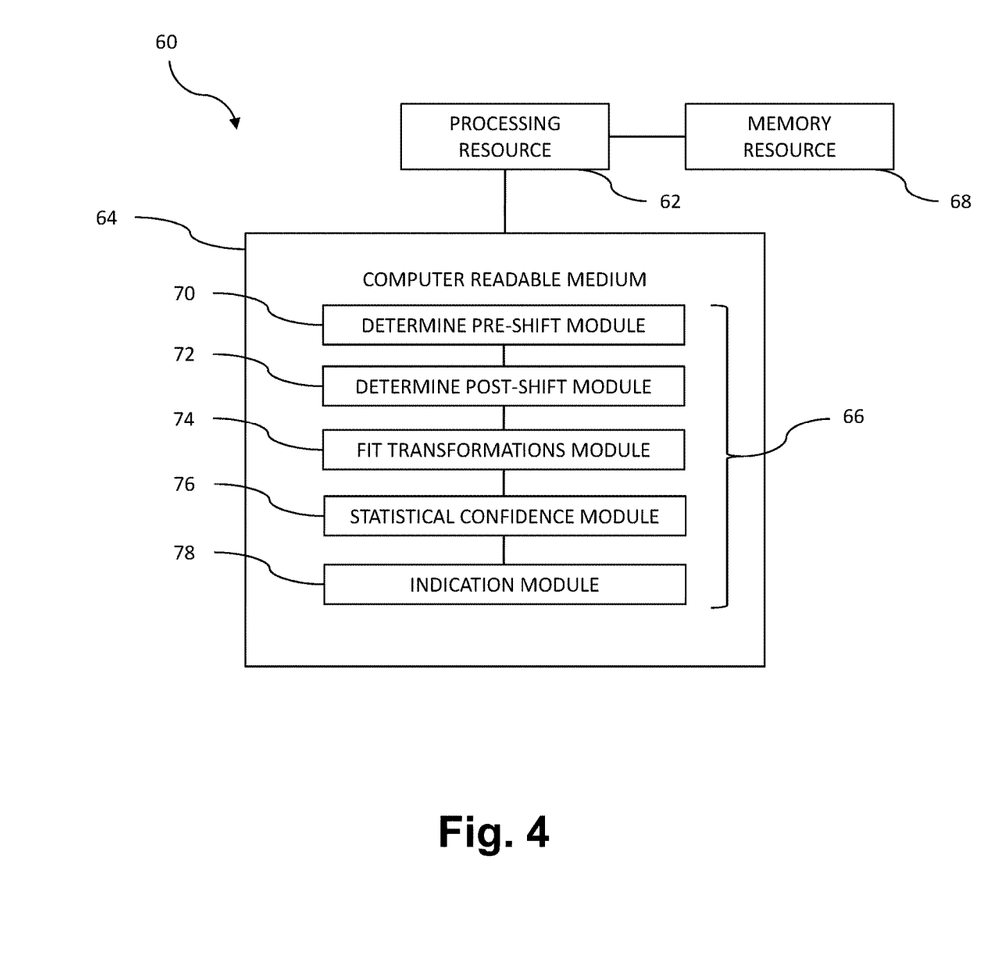
FIG. 4 depicts a block diagram of an example of a computer-readable medium in communication with processing resources of a computing device, in accordance with embodiments of the present disclosure.

FIG. 4 depicts a block diagram of an example of a computer-readable medium in communication with processing resources of a computing device 60, in accordance with embodiments of the present disclosure. The main control 12, as discussed in relation to FIG. 1, can include and/or or be in communication with a computing device, such as that depicted in FIG. 3. The computing device 60 can utilize software, hardware, firmware, and/or logic to perform a number of functions. The computing device 60 can include a number of remote computing devices.

The computing device 60 can be a combination of hardware and program instructions configured to perform a number of functions. The hardware, for example, can include one or more processing resources 62, computer readable medium (CRM) 64, etc. The program instructions (e.g., computer-readable instructions (CRI) 66) can include instructions stored on CRM 64 and executable by the processing resource 62 to implement a desired function (e.g., determine, with a particular statistical confidence, whether the pre-shift transformation differs from the post-shift transformation by a particular threshold distance at a current location of the medical device, etc.). The CRI 66 can also be stored in remote memory managed by a server and represent an installation package that can be downloaded, installed, and executed. The computing device 60 can include memory resources 68, and the processing resources 62 can be coupled to the memory resources 68.

Processing resources 62 can execute CRI 66 that can be stored on an internal or external non-transitory CRM 64. The processing resources 62 can execute CRI 66 to perform various functions, including those function described herein (e.g., steps associated with method flow diagram 40).

A number of modules 70, 72, 74, 76, 78 can be sub-modules or other modules. For example, the determine pre-shift module 70 and the determine post-shift module 72 can be sub-modules and/or contained within a single module. Furthermore, the number of modules 70, 72, 74, 76, 78 can comprise individual modules separate and distinct from one another.

A determine pre-shift module 70 can comprise CRI 66 and can be executed by the processing resource 62 to determine a pre-shift set of fiducial locations associated with a medical device. In some embodiments, position signals can be received from a magnetic position sensor and impedance based sensor disposed on a medical device and a pre-shift fiducial impedance location and a pre-shift fiducial magnetic location can be determined based on the received position signals, respectively. As previously discussed, in some embodiments, the pre-shift time period can exclude a most recent time period.

A determine post-shift module 72 can comprise CRI 66 and can be executed by the processing resource 62 to determine a post-shift set of fiducial locations associated with a medical device. In some embodiments, position signals can be received from a magnetic position sensor and impedance based sensor disposed on a medical device and a post-shift fiducial impedance location and a post-shift fiducial magnetic location can be determined based on the received position signals, respectively. As previously discussed, in some embodiments, the post-shift time period can include a time period that abuts a current time.

A fit transformations module 74 can comprise CRI 66 and can be executed by the processing resource 62 to fit a pre-shift transformation to the pre-shift set of fiducial locations and a post-shift transformation to the post-shift set of fiducial locations. In some embodiments, transformation pairs can be determined for the pre-shift set of fiducials (e.g., data set) and the post-shift set of fiducials (e.g., data set), as previously discussed.

A statistical confidence module 76 can comprise CRI 66 and can be executed by the processing resource 62 to determine, with a particular statistical confidence, whether the pre-shift transformation differs from the post-shift transformation by a particular threshold distance at a current location of the medical device. In some embodiments, the current location of the medical device can be determined based on a signal from a magnetic position sensor disposed on the medical device.

An indication module 78 can comprise CRI 66 and can be executed by the processing resource 62 to determine whether to generate an indication that an impedance shift has occurred, based on the particular statistical confidence of the determined difference. In some embodiments, the statistical confidence can be pre-set and/or user configurable. The statistical confidence can be set to a particular confidence interval that the pre-shift transformation does not differ from the post-shift transformation by more than the particular threshold distance.

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment for impedance shift detection has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed:

1. A computer implemented method for detection of an impedance shift, comprising:
   determining a pre-shift set of fiducials that includes for each fiducial a pre-shift fiducial impedance location and a pre-shift fiducial magnetic location, the pre-shift fiducial impedance locations and the pre-shift fiducial magnetic locations being associated with a medical device;
   determining a post-shift set of fiducials that includes for each fiducial a post-shift fiducial impedance location and a post-shift fiducial magnetic location, the post-shift fiducial impedance locations and the post-shift fiducial magnetic locations being associated with the medical device;
   fitting a pre-shift transformation to the pre-shift set of fiducials and a post-shift transformation to the post-shift set of fiducials;
   determining that a distance, at a current location of the medical device, between the pre-shift transformation and the post-shift transformation exceeds a threshold distance;
   determining a statistical confidence that the distance exceeds the threshold distance;
   determining that the statistical confidence exceeds a threshold confidence;
   determining that the impedance shift has occurred based on the distance exceeding the threshold distance and the statistical confidence exceeding the threshold confidence; and
   generating an indication that the impedance shift has occurred.

2. The method of claim 1, wherein the particular statistical confidence is user configurable.

3. The method of claim 1, wherein the threshold distance is user configurable.

4. The method of claim 1, wherein the pre-shift set of fiducials is collected during a pre-shift time period.

5. The method of claim 4, wherein the pre-shift time period excludes a most recent time period.

6. The method of claim 1, wherein the post-shift set of fiducials is collected during a post-shift time period.

7. The method of claim 6, wherein the post-shift time period includes a time period that abuts a current time.

8. The method of claim 1, wherein the pre-shift set of fiducials is filtered for bad status bits.

9. The method of claim 1, wherein the pre-shift set of fiducials is gated for a particular respiratory phase.

10. The method of claim 1, further comprising providing a notification of the impedance shift to a user via a user interface.

11. The method of claim 1, further comprising determining a time at which the impedance shift has occurred.

12. The method of claim 11, further comprising preventing an additional impedance shift from being reported within a defined time after the time at which the impedance shift has occurred.

13. A system for determining a detection of an impedance shift, comprising:
   a computing device comprising processor resources and memory resources, the memory resources storing computer-readable instructions that, when executed by the processor resources, cause the processor resources to:
   determine a pre-shift set of fiducials that includes for each fiducial a pre-shift fiducial impedance location and a pre-shift fiducial magnetic location, the pre-shift fiducial impedance locations and the pre-shift fiducial magnetic locations being associated with a medical device;
   determine a post-shift set of fiducials that includes for each fiducial a post-shift fiducial impedance location and a post-shift fiducial magnetic location, the post-shift fiducial impedance locations and the post-shift fiducial magnetic locations being associated with the medical device;
   fit a pre-shift transformation to the pre-shift set of fiducials and a post-shift transformation to the post-shift set of fiducials;
   determine that a distance, at a current location of the medical device, between the pre-shift transformation and the post-shift transformation exceeds a threshold distance;
   determine a statistical confidence that the distance exceeds the threshold distance;
   determine that the statistical confidence exceeds a threshold confidence;
   determine that an impedance shift has occurred, based on the distance exceeding the threshold distance and the statistical confidence exceeding the threshold confidence; and
   generate the indication that the impedance shift has occurred.

14. The system of claim 13, wherein the pre-shift set of fiducials associated with the medical device include a pre-shift fiducial impedance location and a pre-shift fiducial magnetic location.

15. The system of claim 13, wherein the post-shift set of fiducials associated with the medical device include a post-shift fiducial impedance location and a post-shift fiducial magnetic location.

16. The system of claim 13, wherein the current location of the medical device is determined based on a signal from a magnetic position sensor disposed on the medical device.

* * * * *